US009695099B2

(12) United States Patent
Liu et al.

(10) Patent No.: US 9,695,099 B2
(45) Date of Patent: Jul. 4, 2017

(54) PROCESS FOR PREPARING ACRYLIC ACID

(71) Applicant: BASF SE, Ludwigshafen am Rhein (DE)

(72) Inventors: Yong Liu, Limburgerhof (DE); Martin Dieterle, Ludwigshafen (DE); Nicolai Tonio Woerz, Darmstadt (DE); Andrei-Nicolae Parvulescu, Ruppertsberg (DE); Michael Lejkowski, Neckargemuend (DE); Johannes Lieberknecht, Limburgerhof (DE); Christian Walsdorff, Ludwigshafen (DE); Kazuhiko Amakawa, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/956,800

(22) Filed: Dec. 2, 2015

(65) Prior Publication Data
US 2016/0152541 A1 Jun. 2, 2016

Related U.S. Application Data

(60) Provisional application No. 62/086,237, filed on Dec. 2, 2014.

(30) Foreign Application Priority Data

Dec. 2, 2014 (DE) .................. 10 2014 017 804

(51) Int. Cl.
*C07C 51/353* (2006.01)
*B01J 27/198* (2006.01)
*B01J 37/08* (2006.01)
*B01J 37/02* (2006.01)
*B01J 23/00* (2006.01)
*B01J 27/199* (2006.01)
*B01J 35/02* (2006.01)
*B01J 37/00* (2006.01)
*B01J 29/70* (2006.01)
*B01J 38/02* (2006.01)

(52) U.S. Cl.
CPC ........... *C07C 51/353* (2013.01); *B01J 23/002* (2013.01); *B01J 27/198* (2013.01); *B01J 27/199* (2013.01); *B01J 29/7057* (2013.01); *B01J 35/023* (2013.01); *B01J 37/0036* (2013.01); *B01J 37/0205* (2013.01); *B01J 37/0213* (2013.01); *B01J 37/08* (2013.01); *B01J 37/0203* (2013.01); *B01J 38/02* (2013.01); *B01J 2523/00* (2013.01)

(58) Field of Classification Search
CPC .... C07C 57/04; C07C 51/353; B01J 29/0358; B01J 27/198
See application file for complete search history.

(56) References Cited

U.S. PATENT DOCUMENTS 4,792,620 A * 12/1988 Paulik ................. B01J 31/0231
560/232
2014/0121403 A1 5/2014 Nagaki et al.

FOREIGN PATENT DOCUMENTS

| DE | 196 27 850 A1 | | 1/1998 |
| EP | 0 616 998 A1 | | 9/1994 |
| JP | 01066141 A | * | 3/1989 |
| WO | WO 2013/117537 A1 | | 8/2013 |
| WO | WO 2014/070735 A1 | | 5/2014 |

OTHER PUBLICATIONS

Ai, Journal of Catalysis, Vapor-Phase Aldol Condensation of Formaldehyde with Acetic Acid on V205-P205 Catalysts, 1987, pp. 201-208.*
Norskov et al, Nature Chemistry, Towards the Computational Design of Solid Catalysts, 2009, 1, pp. 37-46.*
International Search Report and Written Opinion issued Feb. 25, 2016 in PCT/EP2015/078330 (with English translation of categories of cited documents).
James F. Vitcha, et al., "Vapor Phase Aldol Reaction" I & EC Product Research and Development, vol. 5, No. 1, Mar. 1966, pp. 50-53.
Mamoru Ai "Vapor-Phase Aldol Condensation of Formaldehyde with Acetic Acid on $V_2O_5$—$P_2O_5$ Catalysts" Journal of Catalysis, vol. 107, No. 1, XP002667283, 1987, pp. 201-208.
Xinzhen Feng, et al., "Renewable production of acrylic acid and its derivative: New insights into the aldol condensation route over the vanadium phosphorous oxides" Journal of Catalysis, vol. 314, No. 4, XP028651440, 2014, pp. 132-141.

* cited by examiner

*Primary Examiner* — Paul A Zucker
(74) *Attorney, Agent, or Firm* — Oblon, McClelland, Maier & Neustadt, L.L.P.

(57) ABSTRACT

The present invention relates to a process for preparing acrylic acid from acetic acid and formaldehyde, which comprises (a) provision of a stream S1 comprising acetic acid and formaldehyde, where the molar ratio of acetic acid to formaldehyde in the stream S1 is in the range from 0.5:1 to 2:1; (b) contacting of the stream S1 with an aldol condensation catalyst comprising vanadium, phosphorus and oxygen to give a stream S2 comprising acrylic acid, where, in (b), the space velocity WHSV is in the range from 0.35 to 7.0 kg/kg/h.

15 Claims, 1 Drawing Sheet

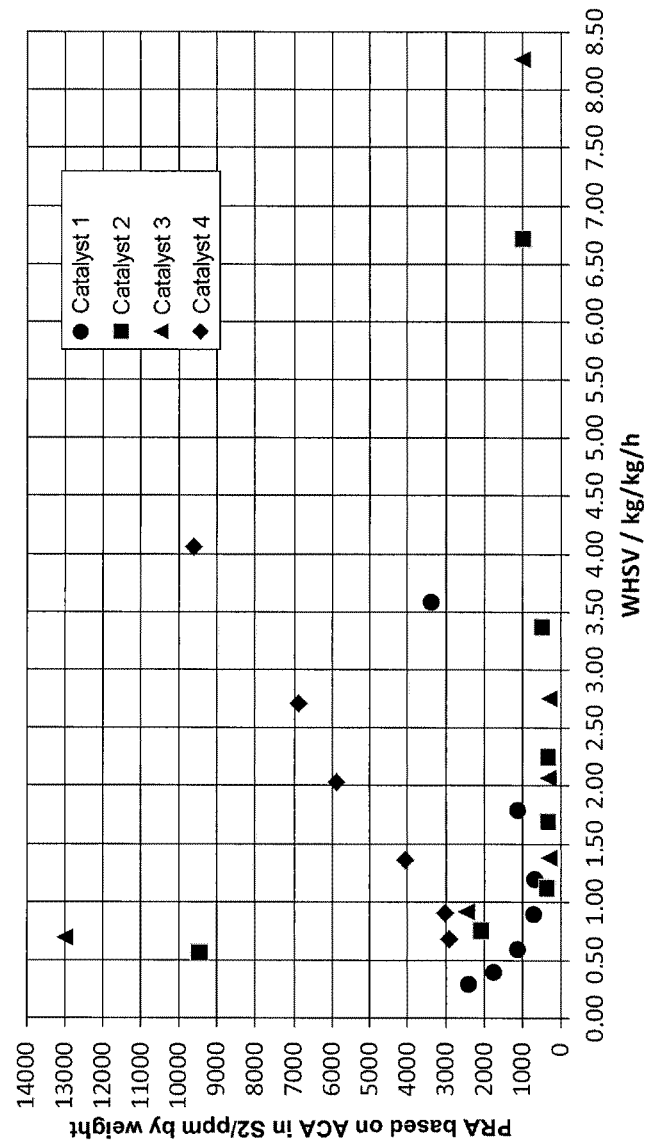

PROCESS FOR PREPARING ACRYLIC ACID

The present invention relates to a process for preparing acrylic acid from acetic acid and formaldehyde. In particular, the present invention relates to a process for preparing acrylic acid having a low content of propionic acid from acetic acid and formaldehyde. The present invention further relates to an aldol condensation catalyst comprising vanadium, phosphorus and oxygen and a process for producing an aldol condensation catalyst.

Acrylic acid is an important monomer for preparing homopolymers and copolymers and is typically obtained by a heterogeneously catalyzed two-stage partial oxidation of propene with acrolein as intermediate.

As an alternative method of preparation, Vitcha and Sims, I & EC Product Research and Development, Vol. 5, No. 1, March 1966, pages 50 to 53, for example, describe the synthesis of acrylic acid in a gas-phase reaction starting out from acetic acid and formaldehyde in an aldol condensation. A problem in the preparation of acrylic acid is the formation of propionic acid (propanoic acid) as by-product and the associated contamination of the acrylic acid, in particular since acrylic acid and propionic acid have virtually the same boiling point. The work-up of acrylic acid and acrylic acid-comprising product streams is thus problematical, especially in respect of the removal of propionic acid as impurity, in particular by means of thermal separation processes, for example by means of distillation.

DE 169 27 850 A1 describes a process for preparing acrylic acid, in which a solvent mixture of a lactam with a polar organic solvent is used for separating off interfering by-products such as propionic acid. To isolate the acrylic acid, the solvent mixture loaded with acrylic acid and by-products has to be subjected to distillation.

EP 0 616 998 A1 states that impurities such as propionic acid present in acrylic acid cannot be removed completely by distillation and therefore proposes a process for purifying acrylic acid by fractional crystallization and thus likewise a removal of propionic acid subsequent to the preparation of acrylic acid.

One of the objects of the present invention was therefore to provide an improved process for preparing acrylic acid from acetic acid and formaldehyde. In particular, one of the objects of the present invention was to provide an improved process for preparing acrylic acid from acetic acid and formaldehyde as a result of which the acrylic acid prepared has such a low quantity of propionic acid that removal of propionic acid so as to meet conventional product specifications of the acrylic acid preferably becomes superfluous.

It has surprisingly been found that such an improved process can be provided by a stream comprising acetic acid and formaldehyde in a specific molar ratio being brought into contact with an aldol condensation catalyst to give a stream comprising acrylic acid, wherein the space velocity WHSV, defined as (mass(formaldehyde)+mass(acetic acid))/mass(aldol condensation catalyst)/time, has a specific value.

The present invention accordingly provides a process which comprises
(a) provision of a stream S1 comprising acetic acid and formaldehyde, where the molar ratio of acetic acid to formaldehyde in the stream S1 is in the range from 0.5:1 to 2:1;
(b) contacting of the stream S1 with an aldol condensation catalyst comprising vanadium, phosphorus and oxygen to give a stream S2 comprising acrylic acid, where, in (b), the space velocity WHSV, defined as (mass(formaldehyde)+mass(acetic acid))/mass(aldol condensation catalyst)/time, is in the range from 0.35 to 7.0 kg/kg/h.

Provision as Per (a)

In step (a) of the process of the invention, a stream S1 comprising acetic acid and formaldehyde, where the molar ratio of acetic acid to formaldehyde in the stream S1 is in the range from 0.5:1 to 2:1, is provided.

The provision as per (a) can, for example, be effected by combining at least one stream comprising acetic acid and at least one stream comprising formaldehyde.

The molar ratio of acetic acid to formaldehyde in the stream S1 is preferably in the range from 0.55:1 to 1.9:1, more preferably from 0.6:1 to 1.8:1, more preferably from 0.65:1 to 1.7:1, more preferably from 0.7:1 to 1.6:1, more preferably from 0.75:1 to 1.5:1, more preferably from 0.8:1 to 1.4:1, more preferably from 0.85:1 to 1.2:1. The molar ratio of acetic acid to formaldehyde in the stream S1 is particularly preferably in the range from 0.9:1 to 1.1:1, for example 1:1.

As source of the acetic acid, it is in principle possible to use any suitable source which comprises at least a proportion of acetic acid. This can be acetic acid freshly introduced into the process. It can likewise be acetic acid which has not been reacted in the above-described process and is, for example after separation from the product stream in one or more work-up steps, recirculated to the process. A combination of acetic acid freshly introduced into the process and acetic acid recirculated to the process is likewise possible.

As source of the formaldehyde, it is likewise possible in principle to use any suitable source which comprises at least a proportion of formaldehyde. This can be formaldehyde freshly introduced into the process. It can likewise be formaldehyde which has not been reacted in the above-described process and is, for example after separation from the product stream in one or more work-up steps, recirculated to the process. A combination of formaldehyde freshly introduced into the process and formaldehyde recirculated to the process is likewise possible. For example, an aqueous formaldehyde solution (formalin) can serve as source of the formaldehyde. It is likewise possible to use a formaldehyde source which supplies formaldehyde, for example trioxane or paraformaldehyde. An aqueous formaldehyde solution preferably serves as source of the formaldehyde. The aqueous formaldehyde solution preferably has a formaldehyde content in the range from 20 to 85% by weight, preferably from 30 to 80% by weight.

In principle, the stream S1 is not restricted in respect of its further composition. It is thus possible for the stream S1 to comprise at least one further component in addition to acetic acid and formaldehyde. The at least one further component is preferably selected from the group consisting of water, oxygen and inert gas or a mixture of at least two or three thereof. The stream S1 more preferably comprises both water and oxygen and inert gas in addition to the acetic acid and the formaldehyde.

For the purposes of the present invention, the term "inert gas" encompasses all materials which are gaseous under the process conditions selected and are inert in both the stages (a) and (b). In this context, inert means that the gaseous material is reacted to an extent of less than 5 mol %, preferably less than 2 mol %, particularly preferably less than 1 mol %, in a single pass through the respective reaction stage. The term "inert gas" as used here refers to either a single gas or a mixture of two or more gases. For example, helium, neon, argon, krypton, xenon, nitrogen, sulfur hexafluoride and mixtures of two or more thereof are possible as inert gases. The inert gas preferably comprises nitrogen, with there being no restrictions in principle in respect of the proportion of nitrogen. If the inert gas comprises nitrogen, preference is given to at least 95% by weight, more preferably at least 98% by weight, more preferably at least 99% by weight, of the inert gas consisting of nitrogen. The inert gas particularly preferably consists of nitrogen. In this context of the present invention, water, carbon monoxide, carbon dioxide, hydrogen, methylene glycol, hemiformal, acetaldehyde, methyl acrylate, methyl acetate, ethene, acetone, methyl formate do not come under the term inert gas.

In principle, the stream S1 is not restricted in respect of its content of acetic acid, formaldehyde, water, oxygen and inert gas. The stream S1 preferably comprises from 50 to 100% by volume, more preferably from 60 to 99.9% by volume, more preferably from 70 to 99.5% by volume, of acetic acid, formaldehyde, water, oxygen and inert gas.

In principle, the stream S1 is not restricted in respect of its acetic acid content and formaldehyde content as long as the molar ratio of acetic acid to formaldehyde in the stream S1 is in the abovementioned ranges. The acetic acid content of the stream S1 is preferably from 4.5 to 36% by volume, more preferably from 5 to 25% by volume, more preferably from 5.5 to 18% by volume, more preferably from 6 to 14% by volume, more preferably from 7 to 11% by volume. The formaldehyde content of the stream S1 is preferably from 4.5 to 36% by volume, more preferably from 5 to 25% by volume, more preferably from 5.5 to 18% by volume, more preferably from 6 to 14% by volume, more preferably from 7 to 11% by volume.

Particular preference is given to the acetic acid content of the stream S1 being from 8 to 10% by volume and the formaldehyde content of the stream S1 being from 8 to 10% by volume.

The water content of the stream S1 is preferably from 7.0 to 50% by volume, more preferably from 8 to 45% by volume, more preferably from 8.5 to 40% by volume, more preferably from 9 to 35% by volume, more preferably from 10 to 25% by volume, more preferably from 11 to 19% by volume. The water content of the stream S1 is particularly preferably from 12 to 18% by volume.

The oxygen content of the stream S1 is preferably from 0.4 to 3% by volume, more preferably from 0.6 to 2.5% by volume, more preferably from 0.8 to 2% by volume, more preferably from 1.2 to 1.8% by volume. The oxygen content of the stream S1 is particularly preferably from 1.3 to 1.7% by volume.

The inert gas content of the stream S1 is preferably from 0.1 to 85% by volume, more preferably from 10 to 82.5% by volume, more preferably from 20 to 80% by volume, more preferably from 40 to 75% by volume, more preferably from 60 to 70% by volume. The inert gas content of the stream S1 is particularly preferably from 63 to 68% by volume.

In principle, the stream S1 is not subject to any particular restriction in respect of further components comprised. Thus, it is possible for the stream S1 to comprise not only acetic acid and formaldehyde and optionally at least one further component selected from the group consisting of water, oxygen, inert gas and a mixture of two or three thereof but also at least one further component. Thus, preference is given to the stream S1 additionally comprising propionic acid. The stream S1 therefore preferably comprises not only acetic acid, formaldehyde, water, oxygen and inert gas but also propionic acid.

The propionic acid content of the stream S1 is preferably up to 2000 ppm by weight, more preferably from 1 to 2000 ppm by weight, more preferably from 5 to 1800 ppm by weight, more preferably from 10 to 1700 ppm by weight.

The stream S1 preferably consists to an extent of from 60 to 99.9% by volume of acetic acid, formaldehyde, water, oxygen, inert gas and propionic acid, where the molar ratio of acetic acid to formaldehyde is in the range from 0.8:1 to 1.4:1, preferably from 0.9:1 to 1.1:1, the acetic acid content is in the range from 8 to 10% by volume, the formaldehyde content is in the range from 8 to 10% by volume, the water content is in the range from 12 to 18% by volume, the oxygen content is in the range from 1.3 to 1.7% by volume, the inert gas content, preferably the nitrogen content, is in the range from 63 to 68% by volume and the propionic acid content is in the range from 10 to 1700 ppm by weight.

The stream S1 can in principle be provided in liquid or gaseous form or in partly liquid and partly gaseous form. The stream S1 is preferably provided in gaseous form.

The stream S1 can in principle be provided at any suitable temperature of the stream. The stream S1 is preferably provided with a temperature of the stream in the range from 150 to 250° C., preferably from 170 to 230° C., preferably from 190 to 210° C., with preferred temperature ranges being, for example, from 190 to 200° C. or from 195 to 205° C. or from 200 to 210° C.

Contacting as Per (b)

In step (b) of the process of the invention, the stream S1 is brought into contact with an aldol condensation catalyst comprising vanadium, phosphorus and oxygen to give a stream S2 comprising acrylic acid.

The Aldol Condensation Catalyst

The term "aldol condensation catalyst" as used in the context of the present invention refers to any catalyst which is able to catalyze an aldol condensation of the two compounds formaldehyde and acetic acid to form acrylic acid.

The form in which vanadium, phosphorus and oxygen are present in the aldol condensation catalyst as per (b) is in principle not restricted.

Vanadium is preferably present as oxygen compound, i.e. as oxide or as oxo anion, in the aldol condensation catalyst as per (b). For the purposes of the present invention, an oxide of a given element X is a compound in which X is bound via one or more covalent bonds to oxygen, with at least part of the valences of X, preferably all valences of X, being covalently bound to oxygen. This applies analogously to the oxo anions of X. As regards the oxo anions, these can in principle be present as salt and/or in protonated form, with any suitable cation or any combination of cations being in principle able to be used as salt. For example, vanadium is therefore present as vanadium(V) oxide $V_2O_5$, vanadium (IV) oxide $VO_2$, vanadium(III) oxide $V_2O_3$, vanadium(II) oxide VO, vanadate $VO_4^{3-}$ or $VO_3^-$, pyrovanadate $V_2O_7^{4-}$, as mixed oxide or as a mixture of at least two thereof.

Phosphorus is preferably present as oxygen compound, i.e. as oxide or as oxo anion, in the aldol condensation catalyst as per (b). For example, phosphorus is therefore present as $P_4O_6$, $P_2O_4$, $P_4O_{10}$, phosphinate, phosphonate, phosphate, hypodiphosphate, diphosphate, hypodiphosphate, diphosphate, polyphosphate, as mixed oxide or as a combination of at least two thereof.

The aldol condensation catalyst preferably comprises vanadium and phosphorus in each case as oxygen compound or as joint oxygen compound, for example as vanadium phosphor oxide, or as a mixture thereof.

The aldol condensation catalyst is in principle not restricted in respect of its contents of vanadium, phosphorus and oxygen.

The content of vanadium in the aldol condensation catalyst is preferably in the range from 2 to 20% by weight, more preferably from 3 to 16% by weight, more preferably from 4 to 14% by weight, more preferably from 4.5 to 8% by weight or from 10 to 13% by weight, more preferably from 5.3 to 6.2% by weight or from 6.3 to 6.9% by weight or from 10.8 to 12.0% by weight, in each case based on the total weight of the aldol condensation catalyst and calculated as elemental V.

The content of phosphorus in the aldol condensation catalyst is preferably in the range from 2 to 20% by weight, more preferably from 3 to 15% by weight, more preferably from 3.5 to 10% by weight, more preferably from 4 to 9% by weight, more preferably from 6 to 8.5% by weight, more preferably from 6.3 to 8.1% by weight, more preferably from 6.4 to 6.6% by weight or from 7.0 to 7.2% by weight or from 7.7 to 7.9% by weight, in each case based on the total weight of the aldol condensation catalyst and calculated as elemental P.

The content of oxygen in the aldol condensation catalyst is preferably in the range from 20 to 60% by weight, more preferably from 30 to 60% by weight, more preferably from 35 to 40% by weight or from 50 to 55% by weight or from 55 to 60% by weight, in each case based on the total weight of the aldol condensation catalyst and calculated as elemental O.

Preference is given to the content of vanadium in the aldol condensation catalyst being in the range from 2 to 20% by weight, that of phosphorus being in the range from 2 to 20% by weight and that of oxygen being in the range from 20 to 60% by weight, in each case based on the total weight of the aldol condensation catalyst. Greater preference is given to the content of vanadium in the aldol condensation catalyst being in the range from 3 to 16% by weight, that of phosphorus being in the range from 3 to 15% by weight and that of oxygen being in the range from 30 to 60% by weight, in each case based on the total weight of the aldol condensation catalyst. Greater preference is given to the content of vanadium in the aldol condensation catalyst being in the range from 4 to 14% by weight, the content of phosphorus being in the range from 3.5 to 10% by weight and that of oxygen being in the range from 30 to 60% by weight, in each case based on the total weight of the aldol condensation catalyst.

The aldol condensation catalyst as per (b) can in principle be present as all-active catalyst or in supported form on at least one support material. If the aldol condensation catalyst is present in supported form, all suitable morphologies resulting from application to a support are possible. Thus, vanadium, phosphorus and oxygen can, for example, be present as a mixture with the at least one support material or be applied as layer to the at least one support material. The aldol condensation catalyst comprising vanadium, phosphorus and oxygen and at least one support material can also have a core-shell structure in which the support material is present in particulate form and the active component comprising vanadium, phosphorus and oxygen at least partly forms a shell structure around this. For the present purposes, a shell or layer also means that the support material has been impregnated with an appropriate solution or plurality of solutions or a suspension or a plurality of suspensions of the active component or one or more precursor compounds and optionally thermally after-treated, for example calcined.

The aldol condensation catalyst as per (b) preferably additionally comprises a support material.

The support material additionally comprised in the aldol concentration catalyst is in principle not subject to any restriction. Possible support materials are therefore all suitable materials known to those skilled in the art which do not influence the active component or active components or influence it/them only to a small extent or only to the extent of the resulting dilution.

The support material is preferably a semimetal oxide or a metal oxide or a mixture thereof or a semimetal-metal mixed oxide. The support material is preferably selected from the group consisting of $SiO_2$, $Al_2O_3$, $ZrO_2$. The support material is particularly preferably $SiO_2$.

The aldol condensation catalyst as per (b) can in principle comprise not only vanadium, phosphorus and oxygen but also at least one further element M. In some embodiments, the aldol condensation catalyst preferably comprises vanadium, phosphorus and oxygen together with at least one further element M selected from the group consisting of Bi, W, Sn, Ti, Fe, Mn, Cr, Cu, K, Cs, Li, Mg and Ca, more preferably selected from the group consisting of Bi, W, Sn and Ti. The aldol concentration catalyst particularly preferably comprises, in some embodiments, vanadium, phosphorus and oxygen together with Bi, W or Bi and W.

The aldol condensation catalyst is in principle not restricted in respect of the content of the at least one further element M. Thus, the content of the at least one further element can be at least 1% by weight, at least 2.5% by weight or at least 5% by weight, in each case based on the total weight of the aldol condensation catalyst. Likewise, the content of the at least one further element can be not more than 60% by weight, not more than 50% by weight or not more than 40% by weight, in each case based on the total weight of the aldol condensation catalyst. The content of the at least one further element is preferably from 2 to 65% by weight, more preferably from 4 to 55% by weight, more preferably from 6 to 45% by weight.

If the element M is bismuth, the content thereof is preferably from 1 to 40% by weight, more preferably from 5 to 35% by weight, more preferably from 7 to 10% by weight or from 28 to 32% by weight. If the element M is tungsten, the content thereof is preferably from 1 to 40% by weight, more preferably from 2.5 to 35% by weight, more preferably from 3.5 to 6.5% by weight or from 28 to 32% by weight, in each case based on the total weight of the aldol condensation catalyst.

The aldol condensation catalyst is in principle not restricted in respect of the molar ratio of vanadium and optionally at least one further element M to phosphorus. The aldol condensation catalyst preferably has a molar ratio of vanadium and the at least one further element (V+M) to phosphorus in the range from 1:4 to 4:1, more preferably from 1:3 to 3:1, more preferably from 1:2.5 to 2.5:1. The aldol condensation catalyst more preferably has a molar ratio of vanadium and the at least one further element (V+M) to phosphorus in the range from 1:2.2 to 1:1.75 or from 1.75:1 to 2.25:1 or from 1:1 to 1:1.5 or from 1.5:1 to 1:2.0.

The aldol condensation catalyst as per (b) is in principle not restricted in respect of the particle size. Thus, it is possible for the aldol condensation catalyst to be present as powder or as shaped body, for example as extrudate, optionally as extrudate comprising a binder material. The aldol condensation catalyst is preferably present as powder. The powder preferably has a particle size distribution, determined in accordance with DIN ISO 3310, in the range from 350 to 500 microns.

In a first particularly preferred embodiment, the aldol condensation catalyst comprises not only vanadium, phosphorus and oxygen but also tungsten, bismuth and $SiO_2$. In this embodiment, the aldol condensation catalyst preferably has a molar ratio of (V+W+Bi) to phosphorus in the range from 1.75:1 to 2.25:1 and the content of vanadium is preferably in the range from 10 to 13% by weight, that of phosphorus is preferably in the range from 5 to 7% by weight, that of oxygen is preferably in the range from 35 to 40% by weight, that of bismuth is preferably in the range from 7 to 10% by weight, that of tungsten is preferably in the range from 29 to 33% by weight and that of silicon is preferably in the range from 4 to 7% by weight, in each case based on the total weight of the aldol condensation catalyst.

Accordingly, the present invention also provides a process for preparing acrylic acid from acetic acid and formaldehyde, which comprises (a) provision of a stream S1 comprising acetic acid and formaldehyde, where the molar ratio of acetic acid to formaldehyde in the stream S1 is in the range from 0.5:1 to 2:1;

(b) contacting of the stream S1 with an aldol condensation catalyst comprising vanadium, phosphorus and oxygen to give a stream S2 comprising acrylic acid, where, in (b), the space velocity WHSV, defined as (mass (formaldehyde)+mass(acetic acid))/mass(aldol condensation catalyst)/time, is in the range from 0.35 to 7.0 kg/kg/h, where the aldol condensation catalyst comprises vanadium, phosphorus and oxygen together with tungsten, bismuth and SiO$_2$, has a molar ratio of (V+W+Bi) to phosphorus in the range from 1.75:1 to 2.25:1 and the content of vanadium is in the range from 10 to 13% by weight, that of phosphorus is in the range from 5 to 7% by weight, that of oxygen is in the range from 35 to 40% by weight, that of bismuth is in the range from 7 to 10% by weight, that of tungsten is in the range from 29 to 33% by weight and that of silicon is in the range from 4 to 7% by weight, in each case based on the total weight of the aldol condensation catalyst, and the stream S1 consists to an extent of from 60 to 99.9% by volume of acetic acid, formaldehyde, water, oxygen and nitrogen, has a molar ratio of acetic acid to formaldehyde of from 0.9:1 to 1.1:1 and the acetic acid content in S1 is from 8 to 10% by volume, the formaldehyde content is from 8 to 10% by volume, the water content is from 12 to 18% by volume, the oxygen content is from 1.3 to 1.7% by volume, the nitrogen content is from 63 to 68% by volume and the propionic acid content is from 10 to 1700 ppm by weight.

In a second particularly preferred embodiment of the present process, the aldol condensation catalyst does not comprise any further element M in addition to vanadium, phosphorus and oxygen and comprises SiO$_2$ as support material. In this embodiment, the aldol condensation catalyst has a molar ratio of vanadium to phosphorus which is preferably in the range from 1:2.2 to 1:1.75 and the content of vanadium in the aldol condensation catalyst is preferably in the range from 5.6 to 6.2% by weight, that of phosphorus is preferably in the range from 6.8 to 7.4% by weight, that of oxygen is preferably in the range from 55 to 60% by weight and that of silicon is preferably in the range from 28 to 30% by weight, in each case based on the total weight of the aldol condensation catalyst.

Accordingly, the present invention also provides a process for preparing acrylic acid from acetic acid and formaldehyde, which comprises (a) provision of a stream S1 comprising acetic acid and formaldehyde, where the molar ratio of acetic acid to formaldehyde in the stream S1 is in the range from 0.5:1 to 2:1;

(b) contacting of the stream S1 with an aldol condensation catalyst comprising vanadium, phosphorus and oxygen to give a stream S2 comprising acrylic acid, where, in (b), the space velocity WHSV, defined as (mass (formaldehyde)+mass(acetic acid))/mass(aldol condensation catalyst)/time, is in the range from 0.35 to 7.0 kg/kg/h, where the aldol condensation catalyst does not comprise any further element M in addition to vanadium, phosphorus and oxygen and comprises SiO$_2$ as support material, has a molar ratio of vanadium to phosphorus in the range from 1:2.2 to 1:1.75 and the content of vanadium is in the range from 5.6 to 6.2% by weight, that of phosphorus is in the range from 6.8 to 7.4% by weight, that of oxygen is in the range from 55 to 60% by weight and that of silicon is in the range from 28 to 30% by weight, in each case based on the total weight of the aldol condensation catalyst, and the stream S1 consists to an extent of from 60 to 99.9% by volume of acetic acid, formaldehyde, water, oxygen and nitrogen, has a molar ratio of acetic acid to formaldehyde of from 0.9:1 to 1.1:1 and the acetic acid content in S1 is from 8 to 10% by volume, the formaldehyde content is from 8 to 10% by volume, the water content is from 12 to 18% by volume, the oxygen content is from 1.3 to 1.7% by volume, the nitrogen content is from 63 to 68% by volume and the propionic acid content is from 10 to 1700 ppm by weight.

In a third particularly preferred embodiment of the present process, the aldol condensation catalyst does not comprise any further element M in addition to vanadium, phosphorus and oxygen and comprises SiO$_2$ as support material. In this embodiment, the aldol condensation catalyst has a molar ratio of vanadium to phosphorus which is preferably in the range from 1:2.2 to 1:1.75 and the content of vanadium is preferably in the range from 6.3 to 6.9% by weight, that of phosphorus is preferably in the range from 7.5 to 8.1% by weight, that of oxygen is preferably in the range from 50 to 55% by weight and that of silicon is preferably in the range from 31 to 33% by weight, in each case based on the total weight of the aldol condensation catalyst.

Accordingly, the present invention also provides a process for preparing acrylic acid from acetic acid and formaldehyde, which comprises (a) provision of a stream S1 comprising acetic acid and formaldehyde, where the molar ratio of acetic acid to formaldehyde in the stream S1 is in the range from 0.5:1 to 2:1;

(b) contacting of the stream S1 with an aldol condensation catalyst comprising vanadium, phosphorus and oxygen to give a stream S2 comprising acrylic acid, where, in (b), the space velocity WHSV, defined as (mass (formaldehyde)+mass(acetic acid))/mass(aldol condensation catalyst)/time, is in the range from 0.35 to 7.0 kg/kg/h, where the aldol condensation catalyst does not comprise any further element M in addition to vanadium, phosphorus and oxygen and comprises SiO$_2$ as support material, has a molar ratio of vanadium to phosphorus in the range from 1:2.2 to 1:1.75 and the content of vanadium is in the range from 6.3 to 6.9% by weight, that of phosphorus is in the range from 7.5 to 8.1% by weight, that of oxygen is in the range from 50 to 55% by weight and that of silicon is in the range from 31 to 33% by weight, in each case based on the total weight of the aldol condensation catalyst, and the stream S1 consists to an extent of from 60 to 99.9% by volume of acetic acid, formaldehyde, water, oxygen and nitrogen, has a molar ratio of acetic acid to formaldehyde of from 0.9:1 to 1.1:1 and the acetic acid content in S1 is from 8 to 10% by volume, the formaldehyde content is from 8 to 10% by volume, the water content is from 12 to 18% by volume, the oxygen content is from 1.3 to 1.7% by volume, the nitrogen content is from 63 to 68% by volume and the propionic acid content is from 10 to 1700 ppm by weight.

In a fourth particularly preferred embodiment of the present process, the aldol condensation catalyst comprises vanadium, phosphorus and oxygen together with tungsten, bismuth and $SiO_2$. In this embodiment, the aldol condensation catalyst has a molar ratio of (V+W+Bi) to phosphorus which is preferably in the range from 1:1 to 1:1.5 and the content of vanadium is preferably in the range from 12.0 to 16.0% by weight, that of phosphorus is preferably in the range from 15.0 to 18.0% by weight, that of oxygen is preferably in the range from 30.0 to 35.0% by weight, that of bismuth is preferably in the range from 28.0 to 35.0% by weight, that of tungsten is preferably in the range from 4.0 to 7.0% by weight and that of silicon is preferably in the range from 2.0 to 4.0% by weight, in each case based on the total weight of the aldol condensation catalyst.

Accordingly, the present invention also provides a process for preparing acrylic acid from acetic acid and formaldehyde, which comprises (a) provision of a stream S1 comprising acetic acid and formaldehyde, where the molar ratio of acetic acid to formaldehyde in the stream S1 is in the range from 0.5:1 to 2:1;

(b) contacting of the stream S1 with an aldol condensation catalyst comprising vanadium, phosphorus and oxygen to give a stream S2 comprising acrylic acid, where, in (b), the space velocity WHSV, defined as (mass (formaldehyde)+mass(acetic acid))/mass(aldol condensation catalyst)/time, is in the range from 0.35 to 7.0 kg/kg/h, where the aldol condensation catalyst comprises vanadium, phosphorus and oxygen together with tungsten and bismuth and $SiO_2$, has a molar ratio of (V+W+Bi) to phosphorus in the range from 1:1 to 1:1.5 and the content of vanadium is in the range from 12.0 to 16.0% by weight, that of phosphorus is in the range from 15.0 to 18.0% by weight, that of oxygen is in the range from 30.0 to 35.0% by weight, that of bismuth is in the range from 28.0 to 35.0% by weight, that of tungsten is in the range from 4.0 to 7.0% by weight and that of silicon is in the range from 2.0 to 4.0% by weight, in each case based on the total weight of the aldol condensation catalyst, and the stream S1 consists to an extent of from 60 to 99.9% by volume of acetic acid, formaldehyde, water, oxygen and nitrogen, has a molar ratio of acetic acid to formaldehyde of from 0.9:1 to 1.1:1 and the acetic acid content in S1 is from 8 to 10% by volume, the formaldehyde content is from 8 to 10% by volume, the water content is from 12 to 18% by volume, the oxygen content is from 1.3 to 1.7% by volume, the nitrogen content is from 63 to 68% by volume and the propionic acid content is from 10 to 1700 ppm by weight.

In a fifth particularly preferred embodiment of the present process, the aldol condensation catalyst comprises vanadium, phosphorus and oxygen together with tungsten, titanium and $SiO_2$. In this embodiment, the aldol condensation catalyst has a molar ratio of (V+W+Ti) to phosphorus which is preferably in the range from 1.5:1 to 1:2.0 and the content of vanadium is preferably in the range from 15.0% to 30.0% by weight, that of phosphorus is preferably in the range from 15.0 to 25.0% by weight, that of oxygen is preferably in the range from 35.0 to 55% by weight, that of titanium is preferably in the range from 0.1 to 12.0% by weight, that of tungsten is preferably in the range from 0.5 to 5.0% by weight and that of silicon is preferably in the range from 2.0 to 4.0% by weight, in each case based on the total weight of the aldol condensation catalyst.

Accordingly, the present invention also provides a process for preparing acrylic acid from acetic acid and formaldehyde, which comprises (a) provision of a stream S1 comprising acetic acid and formaldehyde, where the molar ratio of acetic acid to formaldehyde in the stream S1 is in the range from 0.5:1 to 2:1;

(b) contacting of the stream S1 with an aldol condensation catalyst comprising vanadium, phosphorus and oxygen to give a stream S2 comprising acrylic acid, where, in (b), the space velocity WHSV, defined as (mass (formaldehyde)+mass(acetic acid))/mass(aldol condensation catalyst)/time, is in the range from 0.35 to 7.0 kg/kg/h, where the aldol condensation catalyst comprises vanadium, phosphorus and oxygen together with tungsten, titanium and $SiO_2$, has a molar ratio of (V+W+Ti) to phosphorus in the range from 1.5:1 to 1:2.0 and the content of vanadium is in the range from 15.0 to 30.0% by weight, that of phosphorus is in the range from 15.0 to 25.0% by weight, that of oxygen is in the range from 35.0 to 55% by weight, that of titanium is in the range from 0.1 to 12.0% by weight, that of tungsten is in the range from 0.5 to 5.0% by weight and that of silicon is in the range from 2.0 to 4.0% by weight, in each case based on the total weight of the aldol condensation catalyst, and the stream S1 consists to an extent of from 60 to 99.9% by volume of acetic acid, formaldehyde, water, oxygen and nitrogen, has a molar ratio of acetic acid to formaldehyde of from 0.9:1 to 1.1:1 and the acetic acid content in S1 is from 8 to 10% by volume, the formaldehyde content is from 8 to 10% by volume, the water content is from 12 to 18% by volume, the oxygen content is from 1.3 to 1.7% by volume, the nitrogen content is from 63 to 68% by volume and the propionic acid content is from 10 to 1700 ppm by weight.

Process Parameters

In step (b) of the process of the invention, the stream S1 is brought into contact with the aldol condensation catalyst comprising vanadium, phosphorus and oxygen, giving the stream S2 comprising acrylic acid. The stream S1 can here be completely gaseous, completely liquid or in a form in which at least one component is gaseous and at least one component is liquid, with two or more liquid phases not being ruled out in principle. The stream S1 in step (b) is preferably completely in gaseous form.

The present process can in principle be carried out at all temperatures at which a stream S2 comprising acrylic acid is obtained. The contacting as per (b) is preferably carried out at a temperature of more than 320° C., more preferably in the range from 320 to 420° C., more preferably from 330 to 415° C., more preferably from 350 to 410° C., more preferably from 360 to 390° C., more preferably from 360 to 380° C. This temperature is the temperature of the stream S1 immediately before it comes into contact with the aldol condensation catalyst, measured by means of a thermocouple (NiCrNi).

The present process can in principle be carried out at all pressures at which a stream S2 comprising acrylic acid is obtained. The contacting as per (b) is preferably carried out at a pressure of from 0.01 to 10 bar, more preferably from 0.02 to 7.5 bar, more preferably from 0.05 to 5 bar. The contacting as per (b) is more preferably carried out at a pressure of from 0.1 to 3.5 bar, more preferably from 0.5 to 2.5 bar, more preferably from 0.75 to 2.0 bar, more preferably from 0.9 to 1.5 bar. All pressures in the context of the present invention are absolute pressures.

The contacting as per (b) is preferably carried out at a temperature of from 320 to 420° C. and a pressure of from 0.01 to 10 bar, more preferably at a temperature of from 350 to 410° C. and a pressure of from 0.05 to 5 bar, more preferably at a temperature of from 360 to 390° C. and a pressure of from 0.9 to 1.5 bar.

The WHSV is preferably selected so that the stream S2 obtained directly from the aldol condensation as per (b) of the present process has a very low propionic acid content, based on the acrylic acid comprised in S2.

The space velocity (weight hourly space velocity, WHSV) in (b) is for the present purposes defined as (mass(formaldehyde)+mass(acetic acid))/mass(aldol condensation catalyst)/time and according to the invention is in the range from 0.35 to 7.0 kg/kg/h. "Mass(formaldehyde)" and "mass(acetic acid)" are for the present purposes the respective mass in the stream S1.

The WHSV in (b) of the process of the invention is preferably in the range from 0.40 to 6.0 kg/kg/h, more preferably from 0.45 to 5.0 kg/kg/h, more preferably from 0.5 to 4.0 kg/kg/h, more preferably from 0.75 to 3.5 kg/kg/h. Furthermore, preference is given to the WHSV being in the range from 0.75 to 1.5 kg/kg/h or from 1.0 to 1.75 kg/kg/h or from 1.25 to 2.0 kg/kg/h or from 1.5 to 2.25 kg/kg/h or from 1.75 to 2.5 kg/kg/h or from 2.0 to 2.75 kg/kg/h or from 2.25 to 3.0 kg/kg/h or from 2.5 to 3.25 kg/kg/h or from 2.75 to 3.5 kg/kg/h. The WHSV is particularly preferably from 0.75 to 3.5 kg/kg/h, more preferably from 1.0 to 3.5 kg/kg/h.

It has surprisingly been found in the context of the present invention that when a specific WHSV is selected, a low content of propionic acid based on acrylic acid can be obtained in the stream S2 obtained directly from (b). Compared to values which are lower and higher than the values preferred for the present purposes for the WHSV, significantly higher contents of propionic acid based on acrylic acid are obtained in (b) in the stream S2 obtained directly from (b).

Preference is therefore given to the WHSV in (b) of the process of the invention being in the range from 0.75 to 3.5 kg/kg/h, in which the stream S2 obtained directly from (b) of the process of the invention has a propionic acid content based on acrylic acid of less than 3000 ppm by weight. Further preference is given to the WHSV being in the range from 1.0 to 3.5 kg/kg/h, in which the stream S2 obtained directly from (b) of the process of the invention has a propionic acid content based on acrylic acid of less than 1200 ppm by weight and for some preferred aldol condensation catalysts of less than 1000 ppm by weight, of less than 750 ppm by weight or even less than 500 ppm by weight.

The contacting as per (b) is therefore preferably carried out at a temperature in the range from 355 to 390° C. and a WHSV of from 0.75 to 3.5 kg/kg/h. The contacting as per (b) is therefore more preferably carried out at a temperature in the range from 360 to 390° C. and a WHSV of from 1.0 to 3.5 kg/kg/h.

The contacting as per (b) is therefore preferably carried out at a temperature in the range from 360 to 390° C. and a WHSV of from 1.0 to 3.5 kg/kg/h, with the aldol condensation catalyst comprising vanadium, phosphorus and oxygen together with tungsten, bismuth and $SiO_2$, having a molar ratio of (V+W+Bi) to phosphorus in the range from 1.75:1 to 2.25:1 and the content of vanadium being in the range from 10 to 13% by weight, that of phosphorus being in the range from 5 to 7% by weight, that of oxygen being in the range from 35 to 40% by weight, that of bismuth being in the range from 7 to 10% by weight, that of tungsten being in the range from 29 to 33% by weight and that of silicon being in the range from 4 to 7% by weight, in each case based on the total weight of the aldol condensation catalyst.

The contacting as per (b) is therefore likewise preferably carried out at a temperature in the range from 360 to 390° C. and a WHSV of from 1.0 to 3.5 kg/kg/h, with the aldol condensation catalyst not comprising any further element M in addition to vanadium, phosphorus and oxygen and comprising $SiO_2$ as support material, having a molar ratio of vanadium to phosphorus in the range from 1:2.2 to 1:1.75 and the content of vanadium being in the range from 5.6 to 6.2% by weight, that of phosphorus being in the range from 6.8 to 7.4% by weight, that of oxygen being in the range from 55 to 60% by weight and that of silicon being in the range from 28 to 30% by weight, in each case based on the total weight of the aldol condensation catalyst.

The contacting as per (b) is therefore likewise preferably carried out at a temperature in the range from 360 to 390° C. and a WHSV of from 1.0 to 3.5 kg/kg/h, with the aldol condensation catalyst not comprising any further element M in addition to vanadium, phosphorus and oxygen and comprising $SiO_2$ as support material, having a molar ratio of vanadium to phosphorus in the range from 1:2.2 to 1:1.75 and the content of vanadium being in the range from 6.3 to 6.9% by weight, that of phosphorus being in the range from 7.5 to 8.1% by weight, that of oxygen being in the range from 50 to 55% by weight and that of silicon being in the range from 31 to 33% by weight, in each case based on the total weight of the aldol condensation catalyst.

The contacting as per (b) is therefore likewise preferably carried out at a temperature in the range from 360 to 390° C. and a WHSV of from 1.0 to 3.5 kg/kg/h, with the aldol condensation catalyst comprising tungsten, bismuth and $SiO_2$ in addition to vanadium, phosphorus and oxygen, having a molar ratio of (V+W+Bi) to phosphorus in the range from 1:1 to 1:1.5 and the content of vanadium being in the range from 12.0 to 16.0% by weight, that of phosphorus being in the range from 15.0 to 18.0% by weight, that of oxygen being in the range from 30.0 to 35.0% by weight, that of bismuth being in the range from 28.0 to 35.0% by weight, that of tungsten being in the range from 4.0 to 7.0% by weight and that of silicon being in the range from 2.0 to 4.0% by weight, in each case based on the total weight of the aldol condensation catalyst.

The contacting as per (b) is therefore likewise preferably carried out at a temperature in the range from 360 to 390° C. and a WHSV of from 1.0 to 3.5 kg/kg/h, with the aldol condensation catalyst comprising tungsten, titanium and $SiO_2$ in addition to vanadium, phosphorus and oxygen, having a molar ratio of (V+W+Ti) to phosphorus in the range from 1.5:1 to 1:2.0 and the content of vanadium being in the range from 15.0 to 30.0% by weight, that of phosphorus being in the range from 15.0 to 25.0% by weight, that of oxygen being in the range from 35.0 to 55% by weight, that of titanium being in the range from 0.1 to 12.0% by weight, that of tungsten being in the range from 0.5 to 5.0% by weight and that of silicon being in the range from 2.0 to 4.0% by weight, in each case based on the total weight of the aldol condensation catalyst.

Particular preference is given to the stream S1 consisting to an extent of from 60 to 99.9% by volume of acetic acid, formaldehyde, water, oxygen and nitrogen, having a molar ratio of acetic acid to formaldehyde of from 0.9:1 to 1.1:1, the acetic acid content being from 8 to 10% by volume, the formaldehyde content being from 8 to 10% by volume, the water content being from 12 to 18% by volume, the oxygen content being from 1.3 to 1.7% by volume, the nitrogen content being from 63 to 68% by volume and the propionic acid content being from 10 to 1700 ppm by weight, with the WHSV being from 0.75 to 3.5 kg/kg/h, more preferably from 1.0 to 3.5 kg/kg/h.

Accordingly, the present invention also provides a process for preparing acrylic acid from acetic acid and formaldehyde, which comprises (a) provision of a stream S1 comprising acetic acid and formaldehyde, where the molar ratio of acetic acid to formaldehyde in the stream S1 is in the range from 0.5:1 to 2:1;

(b) contacting of the stream S1 with an aldol condensation catalyst comprising vanadium, phosphorus and oxygen to give a stream S2 comprising acrylic acid, where, in (b), the space velocity WHSV, defined as (mass (formaldehyde)+mass(acetic acid))/mass(aldol condensation catalyst)/time, is in the range from 0.35 to 7.0 kg/kg/h, where the aldol condensation catalyst comprises vanadium, phosphorus and oxygen together with tungsten, bismuth and $SiO_2$, has a molar ratio of (V+W+Bi) to phosphorus in the range from 1.75:1 to 2.25:1 and the content of vanadium is in the range from 10 to 13% by weight, that of phosphorus is in the range from 5 to 7% by weight, that of oxygen is in the range from 35 to 40% by weight, that of bismuth is in the range from 7 to 10% by weight, that of tungsten is in the range from 29 to 33% by weight and that of silicon is in the range from 4 to 7% by weight, in each case based on the total weight of the aldol condensation catalyst, and the stream S1 consists to an extent of from 50 to 99.9% by volume of acetic acid, formaldehyde, water, oxygen and nitrogen, has a molar ratio of acetic acid to formaldehyde of from 0.9:1 to 1.1:1 and the acetic acid content in S1 is from 8 to 10% by volume, the formaldehyde content is from 8 to 10% by volume, the water content is from 12 to 18% by volume, the oxygen content is from 1.3 to 1.7% by volume, the nitrogen content is from 63 to 68% by volume and the propionic acid content is from 10 to 1700 ppm by weight, with the contacting as per (b) being carried out at a temperature in the range from 360 to 390° C. and a WHSV of from 1.0 to 3.5 kg/kg/h.

Accordingly, the present invention also provides a process for preparing acrylic acid from acetic acid and formaldehyde, which comprises (a) provision of a stream S1 comprising acetic acid and formaldehyde, where the molar ratio of acetic acid to formaldehyde in the stream S1 is in the range from 0.5:1 to 2:1;

(b) contacting of the stream S1 with an aldol condensation catalyst comprising vanadium, phosphorus and oxygen to give a stream S2 comprising acrylic acid, where, in (b), the space velocity WHSV, defined as (mass (formaldehyde)+mass(acetic acid))/mass(aldol condensation catalyst)/time, is in the range from 0.35 to 7.0 kg/kg/h, where the aldol condensation catalyst does not comprise any further element M in addition to vanadium, phosphorus and oxygen and comprises $SiO_2$ as support material, has a molar ratio of vanadium to phosphorus in the range from 1:2.2 to 1:1.75 and the content of vanadium is in the range from 5.6 to 6.2% by weight, that of phosphorus is in the range from 6.8 to 7.4% by weight, that of oxygen is in the range from 55 to 60% by weight and that of silicon is in the range from 28 to 30% by weight, in each case based on the total weight of the aldol condensation catalyst, and the stream S1 consists to an extent of from 50 to 99.9% by volume of acetic acid, formaldehyde, water, oxygen and nitrogen, has a molar ratio of acetic acid to formaldehyde of from 0.9:1 to 1.1:1 and the acetic acid content in S1 is from 8 to 10% by volume, the formaldehyde content is from 8 to 10% by volume, the water content is from 12 to 18% by volume, the oxygen content is from 1.3 to 1.7% by volume, the nitrogen content is from 63 to 68% by volume and the propionic acid content is from 10 to 1700 ppm by weight, with the contacting as per (b) being carried out at a temperature in the range from 360 to 390° C. and a WHSV of from 1.0 to 3.5 kg/kg/h.

Accordingly, the present invention also provides a process for preparing acrylic acid from acetic acid and formaldehyde, which comprises (a) provision of a stream S1 comprising acetic acid and formaldehyde, where the molar ratio of acetic acid to formaldehyde in the stream S1 is in the range from 0.5:1 to 2:1;

(b) contacting of the stream S1 with an aldol condensation catalyst comprising vanadium, phosphorus and oxygen to give a stream S2 comprising acrylic acid, where, in (b), the space velocity WHSV, defined as (mass (formaldehyde)+mass(acetic acid))/mass(aldol condensation catalyst)/time, is in the range from 0.35 to 7.0 kg/kg/h, where the aldol condensation catalyst does not comprise any further element M in addition to vanadium, phosphorus and oxygen and comprises $SiO_2$ as support material, has a molar ratio of vanadium to phosphorus in the range from 1:2.2 to 1:1.75 and the content of vanadium is in the range from 6.3 to 6.9% by weight, that of phosphorus is in the range from 7.5 to 8.1% by weight, that of oxygen is in the range from 50 to 55% by weight and that of silicon is in the range from 31 to 33% by weight, in each case based on the total weight of the aldol condensation catalyst, and the stream S1 consists to an extent of from 50 to 99.9% by volume of acetic acid, formaldehyde, water, oxygen and nitrogen, has a molar ratio of acetic acid to formaldehyde of from 0.9:1 to 1.1:1 and the acetic acid content in S1 is from 8 to 10% by volume, the formaldehyde content is from 8 to 10% by volume, the water content is from 12 to 18% by volume, the oxygen content is from 1.3 to 1.7% by volume, the nitrogen content is from 63 to 68% by volume and the propionic acid content is from 10 to 1700 ppm by weight, with the contacting as per (b) being carried out at a temperature in the range from 360 to 390° C. and a WHSV of from 1.0 to 3.5 kg/kg/h.

Accordingly, the present invention also provides a process for preparing acrylic acid from acetic acid and formaldehyde, which comprises (a) provision of a stream S1 comprising acetic acid and formaldehyde, where the molar ratio of acetic acid to formaldehyde in the stream S1 is in the range from 0.5:1 to 2:1;

(b) contacting of the stream S1 with an aldol condensation catalyst comprising vanadium, phosphorus and oxygen to give a stream S2 comprising acrylic acid, where, in (b), the space velocity WHSV, defined as (mass (formaldehyde)+mass(acetic acid))/mass(aldol condensation catalyst)/time, is in the range from 0.35 to 7.0 kg/kg/h, where the aldol condensation catalyst comprises vanadium, phosphorus and oxygen together with tungsten, bismuth and $SiO_2$, has a molar ratio of (V+W+Bi) to phosphorus in the range from 1:1 to 1:1.5 and the content of vanadium is in the range from 12.0 to 16.0% by weight, that of phosphorus is in the range from 15.0 to 18.0% by weight, that of oxygen is in the range from 30.0 to 35.0% by weight, that of bismuth is in the range from 28.0 to 35.0% by weight, that of tungsten is in the range from 4.0 to 7.0% by weight and that of silicon is in the range from 2.0 to 4.0% by weight, in each case based on the total weight of the aldol condensation catalyst, and the stream S1 consists to an extent of from 50 to 99.9% by volume of acetic acid, formaldehyde, water, oxygen and nitrogen, has a molar ratio of acetic acid to formaldehyde of from 0.9:1 to 1.1:1 and the acetic acid content in S1 is from 8 to 10% by volume, the formaldehyde content is from 8 to 10% by volume, the water content is from 12 to 18% by volume, the oxygen content is from 1.3 to 1.7% by volume, the nitrogen content is from 63 to 68% by volume and the propionic acid content is from 10 to 1700 ppm by weight,
with the contacting as per (b) being carried out at a temperature in the range from 360 to 390° C. and a WHSV of from 1.0 to 3.5 kg/kg/h.

Accordingly, the present invention also provides a process for preparing acrylic acid from acetic acid and formaldehyde, which comprises
(a) provision of a stream S1 comprising acetic acid and formaldehyde, where the molar ratio of acetic acid to formaldehyde in the stream S1 is in the range from 0.5:1 to 2:1;
(b) contacting of the stream S1 with an aldol condensation catalyst comprising vanadium, phosphorus and oxygen to give a stream S2 comprising acrylic acid,
where, in (b), the space velocity WHSV, defined as (mass (formaldehyde)+mass(acetic acid))/mass(aldol condensation catalyst)/time, is in the range from 0.35 to 7.0 kg/kg/h, where the aldol condensation catalyst comprises vanadium, phosphorus and oxygen together with tungsten, titanium and $SiO_2$, has a molar ratio of (V+W+Ti) to phosphorus in the range from 1.5:1 to 1:2.0 and the content of vanadium is in the range from 15.0 to 30.0% by weight, that of phosphorus is in the range from 15.0 to 25.0% by weight, that of oxygen is in the range from 35.0 to 55% by weight, that of titanium is in the range from 0.1 to 12.0% by weight, that of tungsten is in the range from 0.5 to 5.0% by weight and that of silicon is in the range from 2.0 to 4.0% by weight, in each case based on the total weight of the aldol condensation catalyst, and the stream S1 consists to an extent of from 50 to 99.9% by volume of acetic acid, formaldehyde, water, oxygen and nitrogen, has a molar ratio of acetic acid to formaldehyde of from 0.9:1 to 1.1:1 and the acetic acid content in S1 is from 8 to 10% by volume, the formaldehyde content is from 8 to 10% by volume, the water content is from 12 to 18% by volume, the oxygen content is from 1.3 to 1.7% by volume, the nitrogen content is from 63 to 68% by volume and the propionic acid content is from 10 to 1700 ppm by weight, with the contacting as per (b) being carried out at a temperature in the range from 360 to 390° C. and a WHSV of from 1.0 to 3.5 kg/kg/h.

The stream S2 comprising acrylic acid which is obtained directly from the aldol condensation as per (b) is in principle not restricted in respect of its composition. The stream S2 preferably comprises water, inert gas and possibly acetic acid, formaldehyde and oxygen in addition to acrylic acid. The stream S2 more preferably comprises water, inert gas, acetic acid, formaldehyde and oxygen in addition to acrylic acid. The stream S2 preferably consists to an extent of at least 50% by volume, preferably at least 55% by volume, more preferably at least 60% by volume, of acrylic acid, water, inert gas and possibly acetic acid, formaldehyde and oxygen, more preferably at least 65% by volume, preferably at least 70% by volume, more preferably at least 75% by volume, of acrylic acid, water, inert gas, acetic acid, formaldehyde and oxygen.

The stream S2 obtained directly from the aldol condensation as per (b) preferably has a low propionic acid content, based on the acrylic acid comprised in S2. The stream S2 obtained directly from the aldol condensation as per (b) preferably comprises not more than 2500 ppm by weight, preferably not more than 2000 ppm by weight, more preferably not more than 1500 ppm by weight, more preferably not more than 1000 ppm by weight, more preferably not more than 750 ppm by weight, more preferably not more than 500 ppm by weight, of propionic acid, based on the acrylic acid comprised in S2.

The propionic acid content of the stream S2 obtained directly from the aldol condensation as per (b) is more preferably from 1 to 2500 ppm by weight, preferably from 1 to 2000 ppm by weight, more preferably from 1 to 1500 ppm by weight, more preferably from 1 to 1000 ppm by weight, more preferably from 1 to 750 ppm by weight, more preferably from 1 to 500 ppm by weight, based on the acrylic acid comprised in S2.

Further Steps

The process of the invention can comprise one or more further steps in addition to the steps (a) and (b). Thus, the process of the invention can additionally comprise the regeneration of the aldol condensation catalyst as per (b), for example by means of a heat treatment. In principle, such a regeneration is carried out when either the conversion of one or more starting materials and/or the selectivity to acrylic acid go below particular values defined in the process design. Furthermore, such a regeneration can be carried out either in the reactor used for the aldol condensation or outside this reactor or partly within and partly outside the reactor.

Work-up

The stream S2 comprising acrylic acid which is obtained as per (b) is in principle not restricted in respect of its further use. Thus, it is possible for the stream S2 to be passed to a work-up or a plurality of work-ups. The one work-up or plurality of work-ups can serve to increase the purity of the resulting acrylic acid further, for example in respect of not only propionic acid but also further by-products of the aldol condensation reaction which are comprised in the stream S2. Likewise, they can serve to separate off one or more components comprised in the stream S2 appropriately and optionally recirculate them at least partly to the process so as to obtain a highly integrated process.

For example, it is possible for the stream S2 to be subjected to one or more thermal separations, preferably one or more distillations, preferably one or more rectifications, for example in order to separate off formaldehyde or water or formaldehyde and water and recirculate them at least partly, optionally after one or more further work-ups, to the process.

The stream S2 obtained as per (b) can in principle have any suitable temperature. The stream S2 obtained as per (b) preferably has a temperature in the range from 320 to 430° C., more preferably in the range from 330 to 420° C. The stream S2 can in principle be used further at the temperature mentioned. Preference is given in the process of the invention to the stream S2 obtained as per (b) being suitably cooled. The heat liberated in this cooling can be utilized appropriately in the process.

It is thus possible for the stream S2 obtained as per (b) to be subjected to intermediate storage, either without prior cooling or after prior cooling as described above, in one or more, preferably one, buffer vessel(s) before being used further. The intermediate storage is preferably carried out, inter alia, to even out possible slight fluctuations in the composition of the stream S2 which can occur during the continuous operation, as is preferred according to the invention, of the overall process and thus ensure that a stream having a comparatively constant composition over time is continuously fed to a downstream process stage. Depending on the design of the overall process, preference is given, for example, to an amount of the stream S2 which is obtained over a period in the range from 1 to 20 hours, preferably from 3 to 15 hours, more preferably from 4 to 12 hours, being subjected to intermediate storage in one or more than one, preferably one, buffer vessel(s). The one or more than one, preferably one, buffer vessel(s) is/are generally maintained at the inflow temperature or a temperature below the inflow temperature.

The stream S2 obtained as per (b) is, optionally after cooling and/or intermediate storage in one or more buffer vessels, preferably fed to a further process stage (c) in order to separate off any water comprised in addition to acrylic acid in the stream S2 and/or any water and formaldehyde comprised from acrylic acid in this at least one process stage in a manner advantageous to the application, which gives a stream S4 enriched in acrylic acid compared to stream S2. Further preference is given to this additional process stage forming not only the stream S4 but also a stream S3 which is depleted in acrylic acid compared to stream S2.

Accordingly, the present invention also provides a process for preparing acrylic acid from acetic acid and formaldehyde which comprises
(a) provision of a stream S1 comprising acetic acid and formaldehyde, where the molar ratio of acetic acid to formaldehyde in the stream S1 is in the range from 0.5:1 to 2:1;
(b) contacting of the stream S1 with an aldol condensation catalyst comprising vanadium, phosphorus and oxygen to give a stream S2 comprising acrylic acid;
(c) removal of at least part of the acrylic acid comprised in S2 to give a stream S3 depleted in acrylic acid compared to S2 and at least one stream S4 enriched in acrylic acid compared to S8;
where, in (b), the space velocity WHSV, defined as (mass (formaldehyde)+mass(acetic acid))/mass(aldol condensation catalyst)/time, is in the range from 0.35 to 7.0 kg/kg/h.

As regards this removal as per (c), it can be carried out by any suitable method or combination of methods. The removal is preferably effected by rectification. The removal by rectification can in principle be carried out using any suitable apparatus or any suitable combination of apparatuses. Preference is here given to using at least one, more preferably one or two, more preferably one, column which according to the invention has separation-active internals. Particular preference is given to using a column which has separation-active internals and is operated as a rectification column; further preference is given to using a column which is operated as a rectification column and is equipped with mass transfer trays as separation-active internals.

In principle, the stream S4 enriched in acrylic acid can be taken off in the stripping section of the column, in the enrichment section of the column or from the bottom of the column. The stream S4 is preferably taken off from the bottom of the column.

The stream S4 is preferably fed to at least one further process stage, with preference being given to obtaining a stream which is further enriched in acrylic acid compared to S4 in this at least one further process stage.

Accordingly, the present invention also provides a process for preparing acrylic acid from acetic acid and formaldehyde which comprises
(a) provision of a stream S1 comprising acetic acid and formaldehyde, where the molar ratio of acetic acid to formaldehyde in the stream S1 is in the range from 0.5:1 to 2:1;
(b) contacting of the stream S1 with an aldol condensation catalyst comprising vanadium, phosphorus and oxygen to give a stream S2 comprising acrylic acid;
(c) removal of at least part of the acrylic acid comprised in S2 to give a stream S3 depleted in acrylic acid compared to S2 and at least one stream S4 enriched in acrylic acid compared to S8;
(d) removal of at least part of the acrylic acid comprised in S4 to give a stream S5 depleted in acrylic acid compared to S4 and at least one stream S6 enriched in acrylic acid compared to S4;
where, in (b), the space velocity WHSV, defined as (mass (formaldehyde)+mass(acetic acid))/mass(aldol condensation catalyst)/time, is in the range from 0.35 to 7.0 kg/kg/h.

As regards the removal as per (d), this can be carried out by any suitable method or combination of methods. The removal as per (d) is preferably carried out by rectification. For the removal by rectification, it is in principle possible to use any suitable apparatus or any suitable combination of apparatuses. Preference is given here to using at least one, more preferably one or two, more preferably one, column(s) which according to the invention has/have separation-active internals. Particular preference is given to using a column which has separation-active internals and is operated as a rectification column; further preference is given to using a column which is operated as a rectification column and is equipped with mass transfer trays, preferably dual-flow trays, as separation-active internals.

Stage (d) gives at least one stream S6 enriched in acrylic acid and/or acrylic acid adducts compared to S4. This at least one stream can consist of one or more individual streams. For the purposes of the present invention, the at least one stream S6 preferably consists of at least two individual streams, more preferably at least the gaseous stream S6a and the liquid stream S6b. As indicated below, these two individual streams are preferably taken off from the stripping section or from the bottom of a column, preferably from the bottom of a column, preferably from the bottom of a rectification column.

The term "acrylic acid adducts" as used in the present context refers to components which are formed reversibly, preferably components which are formed reversibly and have a higher boiling point at atmospheric pressure than acrylic acid, which are formed by dimerization or oligomerization of acrylic acid.

The stream S6a can in principle be taken off in the stripping section of the column, in the enrichment section of the column or from the bottom of the column. The stream S6a is preferably taken off as a side offtake stream, preferably as a gaseous side offtake stream, from the column, more preferably as a gaseous side offtake stream in the stripping section of the column.

In principle, the stream S6a taken off as gaseous side offtake stream in the stripping section of the column from the column as per (d) is not restricted in respect of its further use. Thus, for example, it is possible to utilize the stream S6a commercially as crude acrylic acid stream, to pass it to a process other than the process of the invention or upgrade it by means of one or more than one further process step(s) to give a pure acrylic acid stream. Possible upgrading operations are, for example, a fine purification by rectification, a crystallization or an azeotropic distillation using one or more than one suitable auxiliary.

The stream S6b taken off in liquid form from the bottom of the column as per (d) can be passed to one or more than one further process step(s) in order to convert any dimers and/or oligomers of acrylic acid present back into acrylic acid. To convert any dimers and/or oligomers of acrylic acid present in the stream S6b back into acrylic acid, it is in principle possible to use any suitable apparatus or any suitable combination of apparatuses. Preference is given here to using at least one, more preferably one or two, more preferably one, column(s) which according to the invention has separation-active internals. Particular preference is given to using a column which has separation-active internals and is operated as a rectification column; further preference is given to using a column which is operated as a rectification column and is equipped with mass transfer trays, preferably dual-flow trays, as separation-active internals.

Aldol Condensation Catalyst

Apart from the above-described process for preparing acrylic acid from acetic acid and formaldehyde, the present invention provides the aldol condensation catalyst comprising vanadium, phosphorus and oxygen which is described above for the contacting as per (b).

Process for Producing an Aldol Condensation Catalyst

Apart from the above-described process for preparing acrylic acid from acetic acid and formaldehyde and the aldol condensation catalyst comprising vanadium, phosphorus and oxygen, the present invention provides a process for producing an aldol condensation catalyst.

The process comprises
(i) provision of a support material;
(ii) provision of a vanadium-comprising aqueous solution;
(iii) impregnation of the support material as per (i) with the vanadium-comprising aqueous solution as per (ii);
(iv) drying of the material obtained as per (iii);
(v) provision of a phosphorus-comprising aqueous solution;
(vi) impregnation of the material obtained as per (iv) with the phosphorus-comprising aqueous solution as per (v);
(vii) drying of the material obtained as per (vi);
(viii) calcination of the material obtained as per (vii).

The support material as per (i) is preferably a semimetal oxide or a metal oxide or a mixture thereof. The support material is preferably selected from the group consisting of $SiO_2$, $Al_2O_3$, $ZrO_2$. The support material is more preferably $SiO_2$.

The provision as per (i) can also comprise comminution of the support material. Possible methods here are all methods which are known to those skilled in the art and are suitable for the present purposes, for example comminution by means of a ball mill or a mortar mill or a pestle and a suitable sieve.

There is in principle no restriction in respect of the vanadium-comprising compound or the vanadium-comprising compounds for producing the vanadium-comprising aqueous solution as per (ii). The vanadium-comprising aqueous solution as per (ii) preferably comprises the vanadium at least partly in the form of vanadium(III) citrate or vanadium(III) oxalate or a mixture thereof.

There is in principle no restriction in respect of the phosphorus-comprising compound or the phosphorus-comprising compounds for producing the phosphorus-comprising aqueous solution as per (v). The phosphorus-comprising aqueous solution as per (v) preferably comprises the phosphorus in the form of phosphoric acid.

The drying as per (iv) and the drying as per (vii) are in principle not subject to any restriction in respect of the temperature of the atmosphere surrounding the material. The drying as per (iv) or the drying as per (vii) or the drying as per (iv) and the drying as per (vii) is/are preferably carried out at a temperature of the atmosphere surrounding the material in the range from 60 to 120° C., more preferably from 65 to 110° C., more preferably from 70 to 90° C.

Likewise, the drying as per (iv) and the drying as per (vii) are in principle not subject to any restriction in respect of duration. The drying as per (iv) or the drying as per (vii) or the drying as per (iv) and the drying as per (vii) is/are preferably carried out for a time of from 0.5 to 40 hours, more preferably from 1 to 18 hours, more preferably from 1.5 to 16.5 hours.

The drying as per (iv) or the drying as per (vii) or the drying as per (iv) and the drying as per (vii) is/are therefore preferably carried out at a temperature of the atmosphere surrounding the material in the range from 60 to 120° C. and for a time of from 0.5 to 40 hours, more preferably at a temperature of the atmosphere surrounding the material in the range from 65 to 110° C. for a time of from 1 to 18 hours.

The drying as per (iv) or the drying as per (vii) or the drying as per (iv) and the drying as per (vii) is/are preferably carried out in a nitrogen atmosphere or in air, more preferably in air.

The material obtained as per (vii) is subjected to at least one calcination step. The calcination as per (viii) is in principle not subject to any restriction. The calcination as per (vii) is preferably carried out at a temperature of the atmosphere surrounding the material in the range from 200 to 500° C., more preferably from 240 to 480° C., more preferably from 250 to 450° C., more preferably from 250 to 270° C., for a time of from 1 to 10 hours, more preferably from 1 to 8 hours, more preferably from 1 to 3 hours, with the heating rate preferably being from 0.1 to 5 K/min, more preferably from 0.75 to 1.25 K/min. The calcination is preferably carried out in an atmosphere of nitrogen or air, more preferably air.

An alternative process for producing an aldol condensation catalyst comprises provision of an acidic aqueous solution, preferably comprising citric acid, and combining of this solution with a bismuth-comprising salt, preferably bismuth(III) acetate, a phosphorus-comprising aqueous solution, preferably comprising phosphoric acid, a diol, preferably ethylene glycol, and silica gel. The process further comprises subsequent addition of a vanadium-comprising salt and a tungsten-comprising salt and also methylcellulose to give a suspension and calcination of the solid obtained from the suspension.

The present invention is illustrated by the following embodiments and combinations of embodiments given by the back-references and references.

1. A process for preparing acrylic acid from acetic acid and formaldehyde, which comprises
   (a) provision of a stream S1 comprising acetic acid and formaldehyde, where the molar ratio of acetic acid to formaldehyde in the stream S1 is in the range from 0.5:1 to 2:1;
   (b) contacting of the stream S1 with an aldol condensation catalyst comprising vanadium, phosphorus and oxygen to give a stream S2 comprising acrylic acid,
   where, in (b), the space velocity WHSV, defined as (mass(formaldehyde)+mass(acetic acid))/mass(aldol condensation catalyst)/time, is in the range from 0.35 to 7.0 kg/kg/h.

2. The process as per embodiment 1, wherein the content of vanadium in the aldol condensation catalyst as per (b) is in the range from 2 to 20% by weight, that of phosphorus is in the range from 2 to 20% by weight and that of oxygen is in the range from 20 to 60% by weight, in each case based on the total weight of the aldol condensation catalyst.

3. The process as per either embodiment 1 or 2, wherein the aldol condensation catalyst as per (b) additionally comprises a support material which is preferably a semimetal oxide or a metal oxide or a mixture thereof, preferably selected from the group consisting of $SiO_2$, $Al_2O_3$, $ZrO_2$, more preferably $SiO_2$.

4. The process as per any of embodiments 1 to 3, wherein the aldol condensation catalyst as per (b) additionally comprises at least one further element M selected from the group consisting of Bi, W, Sn, Ti, Fe, Mn, Cr, Cu, K, Cs, Li, Mg and Ca, preferably selected from the group consisting of Bi, W, Sn and Ti.

5. The process as per any of embodiments 1 to 4, wherein the aldol condensation catalyst as per (b) has a molar ratio of vanadium and the at least one further element which is optionally comprised (V+M) to phosphorus in the range from 1:4 to 4:1, preferably from 1:2.5 to 2.5:1.

6. The process as per any of embodiments 1 to 5, wherein the aldol condensation catalyst as per (b) is present as a powder and preferably has a particle size distribution determined in accordance with DIN ISO 3310 in the range from 350 to 500 microns.

7. The process as per any of embodiments 1 to 6, wherein the aldol condensation catalyst as per (b) does not comprise any further element M in addition to vanadium, phosphorus and oxygen and comprises $SiO_2$ as support material, has a molar ratio of vanadium to phosphorus in the range from 1:2 to 1:1.75 and the content of vanadium is in the range from 5.6 to 6.2% by weight, that of phosphorus is in the range from 6.8 to 7.4% by weight, that of oxygen is in the range from 55 to 60% by weight and that of silicon is in the range from 28 to 30% by weight, in each case based on the total weight of the aldol condensation catalyst.

8. The process as per any of embodiments 1 to 6, wherein the aldol condensation catalyst as per (b) does not comprise any further element M in addition to vanadium, phosphorus and oxygen and comprises $SiO_2$ as support material, has a molar ratio of vanadium to phosphorus in the range from 1:2 to 1:1.75 and the content of vanadium is in the range from 6.3 to 6.9% by weight, that of phosphorus is in the range from 7.5 to 8.1% by weight, that of oxygen is in the range from 50 to 55% by weight and that of silicon is in the range from 31 to 33% by weight, in each case based on the total weight of the aldol condensation catalyst.

9. The process as per any of embodiments 1 to 6, wherein the aldol condensation catalyst as per (b) comprises vanadium, phosphorus and oxygen together with tungsten and bismuth, additionally comprises $SiO_2$, has a molar ratio of (V+W+Bi) to phosphorus in the range from 1.75:1 to 2.25:1 and the content of vanadium is in the range from 10 to 13% by weight, that of phosphorus is in the range from 5 to 7% by weight, that of oxygen is in the range from 35 to 40% by weight, that of bismuth is in the range from 7 to 10% by weight, that of tungsten is in the range from 7 to 10% by weight and that of silicon is in the range from 4 to 7% by weight, in each case based on the total weight of the aldol condensation catalyst.

10. The process as per any of embodiments 1 to 6, wherein the aldol condensation catalyst comprises vanadium, phosphorus and oxygen together with tungsten and bismuth and $SiO_2$, has a molar ratio of (V+W+Bi) to phosphorus in the range from 1:1 to 1:1.5 and the content of vanadium is in the range from 12.0 to 16.0% by weight, that of phosphorus is in the range from 15.0 to 18.0% by weight, that of oxygen is in the range from 30.0 to 35.0% by weight, that of bismuth is in the range from 28.0 to 35.0% by weight, that of tungsten is in the range from 4.0 to 7.0% by weight and that of silicon is in the range from 2.0 to 4.0% by weight, in each case based on the total weight of the aldol condensation catalyst.

11. The process as per any of embodiments 1 to 6, wherein the aldol condensation catalyst comprises vanadium, phosphorus and oxygen together with tungsten, titanium and $SiO_2$, has a molar ratio of (V+W+Ti) to phosphorus in the range from 1.5:1 to 1:2.0 and the content of vanadium is in the range from 15.0 to 30.0% by weight, that of phosphorus is in the range from 15.0 to 25.0% by weight, that of oxygen is in the range from 35.0 to 55% by weight, that of titanium is in the range from 0.1 to 12.0% by weight, that of tungsten is in the range from 0.5 to 5.0% by weight, and that of silicon is in the range from 2.0 to 4.0% by weight, in each case based on the total weight of the aldol condensation catalyst.

12. The process as per any of embodiments 1 to 11, wherein the space velocity WHSV in (b) is in the range from 0.4 to 5.0 kg/kg/h, more preferably from 0.5 to 4.0 kg/kg/h, more preferably from 0.75 to 3.5 kg/kg/h, more preferably from 1.0 to 3.5 kg/kg/h.

13. The process as per any of embodiments 1 to 12, wherein the molar ratio of acetic acid to formaldehyde in the stream S1 is in the range from 0.75:1 to 1.5:1, preferably from 0.9:1 to 1.1:1.

14. The process as per any of embodiments 1 to 13, wherein the stream S1 comprises at least one further component, preferably selected from the group consisting of water, oxygen and inert gas, in addition to acetic acid and formaldehyde.

15. The process as per any of embodiments 1 to 14, wherein the stream S1 comprises water, oxygen and inert gas in addition to acetic acid and formaldehyde.

16. The process as per embodiment 15, wherein the stream S1 consists to an extent of from 50 to 100% by volume, preferably from 60 to 99.9% by volume, of acetic acid, formaldehyde, water, oxygen and inert gas.

17. The process as per either embodiment 15 or 16, wherein the acetic acid content of the stream S1 is from 4.5 to 36% by volume and the formaldehyde content of the stream S1 is from 4.5 to 36% by volume.

18. The process as per any of embodiments 15 to 17, wherein the water content of the stream S1 is from 7.0 to 50.0% by volume, preferably from 12 to 18% by volume.

19. The process as per any of embodiments 15 to 18, wherein the oxygen content of the stream S1 is from 0.4 to 3% by volume, preferably from 1.3 to 1.7% by volume.

20. The process as per any of embodiments 15 to 19, wherein the inert gas content of the stream S1 is from 0.1 to 85.0% by volume, preferably from 63 to 68% by volume.

21. The process as per any of embodiments 15 to 20, wherein the inert gas in the stream S1 comprises nitrogen, with preference being given to at least 95% by weight, more preferably at least 98% by weight, more preferably at least 99% by weight, of the inert gas consisting of nitrogen.

22. The process as per any of embodiments 15 to 21, wherein the stream S1 additionally comprises propionic acid, with the propionic acid content of the stream S1 preferably being from 1 to 2000 ppm by weight, more preferably from 5 to 1800 ppm by weight, more preferably from 10 to 1700 ppm by weight.

23. The process as per any of embodiments 1 to 22, wherein the stream S1 provided as per (a) is in gaseous form.

24. The process as per any of embodiments 1 to 23, wherein the stream S1 is provided with a temperature in the range from 150 to 250° C., preferably from 170 to 230° C., preferably from 190 to 210° C.
25. The process as per any of embodiments 1 to 24, wherein the contacting as per (b) is carried out at a temperature of the catalyst bed of more than 320° C., preferably in the range from 320 to 420° C., preferably from 350 to 410° C.
26. The process as per any of embodiments 1 to 25, wherein the stream S2 obtained directly from the aldol condensation comprises not more than 2500 ppm by weight of propionic acid, preferably not more than 2000 ppm by weight, more preferably not more than 1500 ppm by weight, more preferably not more than 1000 ppm by weight, more preferably not more than 750 ppm by weight, more preferably not more than 500 ppm by weight, based on the acrylic acid comprised in S2.
27. The process as per any of embodiments 1 to 26, wherein the propionic acid content of the stream S2 obtained directly from the aldol condensation is from 1 to 2500 ppm by weight, preferably from 1 to 2000 ppm by weight, more preferably from 1 to 1500 ppm by weight, more preferably from 1 to 1000 ppm by weight, more preferably from 1 to 750 ppm by weight, more preferably from 1 to 500 ppm by weight, based on the acrylic acid comprised in S2.
28. An aldol condensation catalyst comprising vanadium, phosphorus and oxygen and $SiO_2$ as support material, wherein the aldol condensation catalyst has a molar ratio of vanadium to phosphorus in the range from 1:2 to 1:1.75 and the content of vanadium is in the range from 5.6 to 6.2% by weight, that of phosphorus is in the range from 6.8 to 7.4% by weight, that of oxygen is in the range from 56.5 to 58.5% by weight and that of silicon is in the range from 28 to 30% by weight, in each case based on the total weight of the aldol condensation catalyst.
29. An aldol condensation catalyst comprising vanadium, phosphorus and oxygen and $SiO_2$ as support material, wherein the aldol condensation catalyst has a molar ratio of vanadium to phosphorus in the range from 1:2 to 1:1.75 and the content of vanadium is in the range from 6.3 to 6.9% by weight, that of phosphorus is in the range from 7.5 to 8.1% by weight, that of oxygen is in the range from 52.5 to 54.5% by weight and that of silicon is in the range from 31 to 33% by weight, in each case based on the total weight of the aldol condensation catalyst.
30. An aldol condensation catalyst comprising vanadium, phosphorus and oxygen together with tungsten, bismuth and $SiO_2$, wherein the aldol condensation catalyst has a molar ratio of (V+W+Bi) to phosphorus in the range from 1.75:1 to 2.25:1 and the content of vanadium is in the range from 10 to 13% by weight, that of phosphorus is in the range from 5 to 7% by weight, that of oxygen is in the range from 35 to 39% by weight, that of bismuth is in the range from 7 to 10% by weight, that of tungsten is in the range from 7 to 10% by weight and that of silicon is in the range from 4 to 7% by weight, in each case based on the total weight of the aldol condensation catalyst.
31. An aldol condensation catalyst comprising vanadium, phosphorus and oxygen together with tungsten and bismuth and $SiO_2$, wherein the aldol condensation catalyst has a molar ratio of (V+W+Bi) to phosphorus in the range from 1:1 to 1:1.5 and the content of vanadium is in the range from 12.0 to 16.0% by weight, that of phosphorus is in the range from 15.0 to 18.0% by weight, that of oxygen is in the range from 30.0 to 35.0% by weight, that of bismuth is in the range from 28.0 to 35.0% by weight, that of tungsten is in the range from 4.0 to 7.0% by weight and that of silicon is in the range from 2.0 to 4.0% by weight, in each case based on the total weight of the aldol condensation catalyst.
32. An aldol condensation catalyst comprising vanadium, phosphorus and oxygen together with tungsten, titanium and $SiO_2$, wherein the aldol condensation catalyst has a molar ratio of (V+W+Ti) to phosphorus in the range from 1.5:1 to 1:2.0 and the content of vanadium is in the range from 15.0 to 30.0% by weight, that of phosphorus is in the range from 15.0 to 25.0% by weight, that of oxygen is in the range from 35.0 to 55% by weight, that of titanium is in the range from 0.1 to 12.0% by weight, that of tungsten is in the range from 0.5 to 5.0% by weight and that of silicon is in the range from 2.0 to 4.0% by weight, in each case based on the total weight of the aldol condensation catalyst.
33. The aldol condensation catalyst as per any of embodiments 28 to 32, wherein the aldol condensation catalyst is present as powder and preferably has a particle size distribution determined in accordance with DIN ISO 3310 in the range from 350 to 500 microns.
34. A process for producing an aldol condensation catalyst, which comprises
(i) provision of a support material;
(ii) provision of a vanadium-comprising aqueous solution;
(iii) impregnation of the support material as per (i) with the vanadium-comprising aqueous solution as per (ii);
(iv) drying of the material obtained as per (iii);
(v) provision of a phosphorus-comprising aqueous solution;
(vi) impregnation of the material obtained as per (iv) with the phosphorus-comprising aqueous solution as per (v);
(vii) drying of the material obtained as per (vi);
(viii) calcination of the material obtained as per (vii).
35. The process as per embodiment 34, wherein the support material as per (i) is a semimetal oxide or a metal oxide or a mixture thereof, preferably selected from the group consisting of $SiO_2$, $Al_2O_3$, $ZrO_2$, more preferably $SiO_2$.
36. The process as per either embodiment 34 or 35, wherein the vanadium-comprising aqueous solution as per (ii) comprises the vanadium at least partly in the form of vanadium(III) citrate or vanadium(III) oxalate or a mixture thereof.
37. The process as per any of embodiments 34 to 36, wherein the phosphorus-comprising aqueous solution as per (v) comprises the phosphorus at least partly in the form of phosphoric acid.
38. The process as per any of embodiments 34 to 37, wherein the drying as per (iv) or the drying as per (vii) or the drying as per (iv) and the drying as per (vii) is/are carried out at a temperature of the atmosphere surrounding the material in the range from 60 to 120° C., preferably from 70 to 90° C.
39. The process as per embodiment 38, wherein the drying as per (iv) or the drying as per (vii) or the drying as per (iv) and the drying as per (vii) is/are carried out for a time of from 0.5 to 40 hours, preferably from 1 to 18 hours.
40. The process as per any of embodiments 34 to 39, wherein the calcination as per (viii) is carried out at a temperature of the atmosphere surrounding the material in the range from 200 to 500° C., preferably from 240 to 480° C., more preferably from 250 to 270° C., and for a time of from 1 to 10 hours, preferably from 1 to 8 hours, more preferably from 1 to 3 hours.
41. An aldol condensation catalyst obtained or obtainable by a process as per any of embodiments 34 to 40.

US Provisional Patent Application No. 62/086,237, filed 2 Dec. 2014, is incorporated into the present application by literature reference. With regard to the abovementioned teachings, numerous changes and deviations from the present invention are possible. It can therefore be assumed that the invention, within the scope of the appended claims, can be performed differently from the way described specifically herein.

DESCRIPTION OF THE FIGURE

FIG. 1 shows a plot of the propionic acid content in ppm by weight in stream S2 based on the acrylic acid comprised in S2 (ordinate) at the respective space velocity WHSV in kg/kg/h, defined as (mass(formaldehyde)+mass(acetic acid))/mass(aldol condensation catalyst)/time (abscissa). The ordinate extends from 0 to 14 000 ppm by weight of propionic acid in stream S2, based on the acrylic acid comprised in S2, and the abscissa extends from 0.00 to 8.50 kg/kg/h. The results for catalyst 1 (●), catalyst 2 (■), catalyst 3 (▲) and catalyst 4 (♦) are shown.

The present invention is illustrated by the following examples.

EXAMPLES

I. Analytical Methods
I.1 Gas Chromatography

The analysis of the gaseous product stream was carried out with the aid of an on-line GCMS system from Agilent. The instrument was equipped with a 10-way valve having two sample loops (500 microliters/1000 microliters) which were operated at 220° C. Detection was effected by means of a flame ionization detector (FID) and two thermal conductivity detectors. For the FID stream introduced through the front inlet, the following parameters were selected: injector temperature: 275° C.; split: 1:5. An FFAP column having a length of 30 m, an internal diameter of 0.32 mm and a film thickness of 0.5 microns (column inflow: 5 ml/min) was used. The sample was fed to the thermal conductivity detectors in parallel through the rear inlet with the aid of a Y-adapter (JAS). Here, the following parameters were selected: injector temperature: 275° C.; split 1:2. For the first thermal conductivity detector, a column of the volamine type having a length of 60 m, an internal diameter of 0.32 mm and a film thickness of 0.45 microns (column flow: 2 ml/min) was used. The second thermal conductivity detector had a column system comprising two columns. First column: RTX5 having a length of 30 m, an internal diameter of 0.32 mm, a film thickness of 1 micron (column flow: 5 ml/min). Second column: "select permanent gases/$CO_2$ HR" having a length of 50 m, an internal diameter of 0.32 mm and a film thickness of 10 microns (column flow: 2 ml/min). All columns were operated using helium as carrier gas. The GC oven temperature program was as follows:
   40° C. (2.5 min hold time)
   heating to 105° C. at a heating rate of 20 K/min (0 min hold time)
   heating to 225° C. at a heating rate of 40 K/min (2.75 min hold time)
I.2 Elemental Analysis The determination of the quantitative composition of the catalysts was carried out by means of wavelength-dispersive X-ray fluorescence analysis.
II. Production of the Catalysts
II.1 Catalyst 1 (BiWVPO)

100 g of citric acid were dissolved in 1000 ml of DI water (deionized water) and heated to 80° C. 67 g of bismuth(III) acetate, 117.6 g of 85% strength by weight aqueous phosphoric acid, 100 g of ethylene glycol, 116 g of Ludox® AS-40 (40% by weight of colloidal $SiO_2$ in water) were added; the mixture obtained was stirred at 80° C. for 30 minutes. 110 g of ammonium metavanadate ($NH_4VO_3$), 169 g of ammonium metatungstate (($NH_4)_6H_2W_{12}O_{40} \cdot xH_2O$) and 20 g of methylcellulose were added, and the suspension was stirred at 80° C. for 3 hours.

Volatile constituents of the suspension were removed at 60° C. and 45 mbar on a rotary evaporator; the powder obtained was dried at 100° C. in a convection drying oven for 16 hours and subsequently calcined according to the following temperature program in a muffle furnace:
10 K/min to 160° C., hold for 2 h;
3 K/min to 250° C., hold for 2 h;
3 K/min to 300° C., hold for 6 h;
3 K/min to 450° C., hold for 6 h.

The material obtained had a bismuth content of 8.5% by weight, a tungsten content of 31% by weight, a vanadium content of 11.4% by weight, a phosphorus content of 6.5% by weight and a silicon content of 5.6% by weight. The difference to 100% by weight corresponds to the oxygen content.

The powder was tableted and then comminuted to 350-500 μm.
II.2 Catalyst 2 (VPO $SiO_2$)

Silica gel (Siliperl AF 125, 3-5 mm balls, manufacturer: BASF) was comminuted to the desired fraction (350-500 microns) and used as support material. 400 g of support material (Siliperl AF 125) was impregnated with 372 ml of 2.0 molar aqueous vanadium(III) citrate solution. The mixture was subsequently dried at 80° C. in a convection drying oven for 16 hours.

168.2 g of 85% strength by weight aqueous phosphoric acid was diluted with DI water to 372 ml, and the above-described, dried material was impregnated therewith. The mixture was subsequently dried at 80° C. in a convection drying oven for 16 hours.

The mixture comprising V and P was calcined according to the following temperature program in a muffle furnace:
1 K/min to 260° C., hold for 2 h.

The material obtained had a vanadium content of 5.9% by weight, a phosphorus content of 7.1% by weight and a silicon content of 29.3% by weight. The difference to 100% by weight corresponds to the oxygen content.
II.3 Catalyst 3 (VPO $SiO_2$)

Silica gel (CARiACT Q-20C, 3-5 mm balls, manufacturer: Fuji Silysia) was comminuted to the desired fraction (350-500 microns) and used as support material. 100 g of support material (CARiACT Q-20C) was impregnated with 84 ml of 2.2 molar aqueous vanadium(III) citrate solution. The mixture was subsequently dried at 80° C. in a convection drying oven for 16 hours.

42 g of 85% strength by weight phosphoric acid were diluted with DI water to 84 ml, and the above-described, dried material was impregnated therewith. The mixture was subsequently dried at 80° C. in a convection drying oven for 16 hours.

The mixture comprising V and P was calcined according to the following temperature program in a muffle furnace:
1 K/min to 260° C., hold for 2 h.

The material obtained had a vanadium content of 6.6% by weight, a phosphorus content of 7.8% by weight and a silicon content of 32.0% by weight. The difference to 100% by weight corresponds to the oxygen content.

II.4 Catalyst 4 (Sn Zeolite)

Deboronized zeolitic material of the structure type BEA was firstly produced as described in "Example 6", sections 6.1 and 6.2, of WO 2013/117537 A1. 50 g of this zeolitic material were placed together with 14.2 g of tin(II) acetate (Sn(OAc)$_2$) in a mixer (Microton MB550 mill) and the mixture was milled for 15 minutes at 14 000 rpm (revolutions per minute). After milling, the mixture was placed in a porcelain dish and calcined at 500° C. for 3 hours under nitrogen, followed by 3 hours in air (heating rate 2 K/min). The material obtained had a tin content of 13.1% by weight, a silicon content of 38% by weight and a total content of organic carbon (TOC) of less than 0.1% by weight.

III. Catalytic Studies

III.1 Procedure

The catalytic studies were in each case carried out on a 1 ml pulverulent sample; a crushed material fraction having a particle size in the range from 0.315 to 0.5 mm was used for this purpose. The WHSV was varied either by adjusting the gas stream S1 or by diluting the respective catalyst as per II with steatite particles (total volume of catalyst and steatite constant at 1 ml). The catalysts as per II, optionally diluted with steatite particles, were positioned in tube reactors between two inert particle beds of crushed fused silica and the loaded tube reactors were installed in the catalysis apparatus (16-fold high-throughput screening plant).

A stream composed of technical-grade formalin (49% formaldehyde solution in water), acetic acid (100% Bernd Kraft, 16873.4000), nitrogen (Praxair, purity 5.0) and oxygen (synthetix air, Praxair, purity max.±10% rel.) was heated to 200° C. (composition of the stream: acetic acid 9% by volume, formaldehyde 9% by volume, water 15% by volume, oxygen 1.5% by volume, nitrogen 65.5% by volume; molar ratio of acetic acid to formaldehyde: 1:1) and thereby vaporized. The gaseous mixture was then brought into contact with an aldol condensation catalyst (350-500 µm) as per II in the form of crushed material at 370° C. and 1.1 bar.

The temperature was measured by means of a thermocouple in the isothermal zone of the reactor, i.e. the catalyst bed, at the beginning of the experiment and corresponds to the temperature at which the reactions were carried out. The product stream was diluted with argon (purity: 5.0) (Ar: product stream=22:1) and the composition was determined by gas chromatography.

The data shown in FIG. 1 and discussed below demonstrate the result found, with the process of the invention being operated for 8 hours.

III.2 Evaluation

The concentration of propionic acid based on acrylic acid ($Con_{PRA}$) in the stream S2 is calculated according to the following formula:

$$Con_{PRA} = 100 * (NC^P_{PRA}/NC^P_{ACA})$$

$NC^P_{PRA}$=number of carbon atoms comprised in the form of propionic acid in the stream S2.

$NC^P_{ACA}$=number of carbon atoms comprised in the form of acrylic acid in the stream S2.

It was surprisingly found in the context of the present invention that when a specific WHSV is selected, a low content of propionic acid based on acrylic acid can be obtained in the stream S2 obtained directly from (b). Especially in the range from 0.75 to 3.5 kg/kg/h, particularly in the range from 1.0 to 3.5 kg/kg/h, the results for the catalysts 1, 2 and 3 display particularly low values for the content of propionic acid based on acrylic acid in the stream S2 obtained directly from (b).

LITERATURE CITED

Vitcha and Sims, I & EC Product Research and Development, Vol. 5, No. 1, March 1966, pages 50 to 53
DE 169 27 850 A1
EP 0 616 998 A1

The invention claimed is:

1. A process for preparing acrylic acid from acetic acid and formaldehyde, the process comprising:
   (a) providing a stream S1 comprising acetic acid and formaldehyde, where a molar ratio of acetic acid to formaldehyde in the stream S1 is from 0.5:1 to 2:1;
   (b) contacting the stream S1 with an aldol condensation catalyst comprising vanadium, phosphorus and oxygen to give a stream S2 comprising acrylic acid,
   wherein, in (b), a space velocity WHSV, defined ([Formaldehyde]+[acetic acid])/[aldol condensation catalyst]/time, is from 0.75 to 3.5 kg/kg/h, wherein [formaldehyde], [acetic acid], and [aldol condensation catalyst] represent mass of formaldehyde, acetic acid, and the aldol condensation catalyst, respectively, and wherein the aldol condensation catalyst in (b) comprises SiO$_2$ as a support material.

2. The process according to claim 1, wherein the content of vanadium in the aldol condensation catalyst as per (b) is from 2 to 20% by weight, the content of phosphorus is from 2 to 20% by weight, and the content of oxygen is from 20 to 60% by weight, in each case based on the total weight of the aldol condensation catalyst.

3. The process according to claim 1, wherein the aldol condensation catalyst in (b) additionally comprises at least one further element M selected from the group consisting of Bi, W, Sn, Ti, Fe, Mn, Cr, Cu, K, Cs, Li, Mg and Ca.

4. The process according to claim 1, wherein the aldol condensation catalyst in (b) is present as a powder.

5. The process according to claim 1, wherein the aldol condensation catalyst in (b)
   does not comprise other elements in addition to vanadium, phosphorus and oxygen,
   has a molar ratio of vanadium to phosphorus of from 1:2 to 1:1.75, and
   the content of vanadium is from 5.6 to 6.2% by weight, the content of phosphorus is from 6.8 to 7.4% by weight, the content of oxygen is from 55 to 60% by weight, and the content of silicon is from 28 to 30% by weight, in each case based on the total weight of the aldol condensation catalyst.

6. The process according to claim 1, wherein the aldol condensation catalyst in (b)
   does not comprise other elements in addition to vanadium, phosphorus and oxygen,
   has a molar ratio of vanadium to phosphorus of from 1:2 to 1:1.75, and
   the content of vanadium is from 6.3 to 6.9% by weight, the content of phosphorus is from 7.5 to 8.1% by weight, the content of oxygen is from 50 to 55% by weight, and the content of silicon is from 31 to 33% by weight, in each case based on the total weight of the aldol condensation catalyst.

7. The process according to claim 1, wherein the aldol condensation catalyst in (b)
   comprises vanadium, phosphorus, oxygen, tungsten, and bismuth,
   has a molar ratio of (V+W+Bi) to phosphorus of from 1.75:1 to 2.25:1, and
   the content of vanadium is from 10 to 13% by weight, the content of phosphorus is from 5 to 7% by weight, the content of oxygen is from 35 to 40% by weight, the content of bismuth is from 7 to 10% by weight, the content of tungsten is from 7 to 10% by weight, and the content of silicon is from 4 to 7% by weight, in each case based on the total weight of the aldol condensation catalyst.

8. The process according to claim 1, wherein the molar ratio of acetic acid to formaldehyde in the stream S1 is from 0.75:1 to 1.5:1.

9. The process according to claim 1, wherein the stream S1 comprises at least one further component in addition to acetic acid and formaldehyde.

10. The process according to claim 9, wherein the at least one further component is selected from the group consisting of water, oxygen and an inert gas.

11. The process according to claim 10, wherein the stream S1 comprises from 50 to 100% by volume of acetic acid, formaldehyde, water, oxygen and the inert gas.

12. The process according to claim 9, wherein the stream S1 additionally comprises propionic acid.

13. The process according to claim 1, wherein the contacting (b) is carried out at a temperature of the catalyst bed of more than 320° C.

14. The process according to claim 1, wherein the stream S2 comprises propionic acid of not more than 2500 ppm by weight based on the acrylic acid comprised in S2.

15. The process according to claim 10, wherein the stream S1 additionally comprises propionic acid.

* * * * *